United States Patent
Polishak et al.

(10) Patent No.: US 9,458,376 B2
(45) Date of Patent: Oct. 4, 2016

(54) ELECTROCHROMIC IPTYCENES

(71) Applicants: Brent M. Polishak, San Ramon, CA (US); David P. Waller, Lexington, MA (US)

(72) Inventors: Brent M. Polishak, San Ramon, CA (US); David P. Waller, Lexington, MA (US)

(*) Notice: Subject to any disclaimer, the term of this patent is extended or adjusted under 35 U.S.C. 154(b) by 0 days.

(21) Appl. No.: 14/547,429

(22) Filed: Nov. 19, 2014

(65) Prior Publication Data

US 2016/0137914 A1 May 19, 2016

(51) Int. Cl.
*C07D 471/18* (2006.01)
*C09K 9/02* (2006.01)
*C07D 471/08* (2006.01)

(52) U.S. Cl.
CPC ............... *C09K 9/02* (2013.01); *C07D 471/08* (2013.01); *C07D 471/18* (2013.01); *C09K 2211/1018* (2013.01)

(58) Field of Classification Search
CPC .................................................. C07D 491/20
USPC .......................................................... 546/34
See application file for complete search history.

(56) References Cited

U.S. PATENT DOCUMENTS

2014/0124762 A1* 5/2014 Buchwald ........... H01L 51/0072
257/40

OTHER PUBLICATIONS

Kohl et al Organic Letters 2014, 16, 704-707.*
Jiang et al Synlett 2010, 11, 1679-1681—abstract.*
Eckstein et al Dissertationes Pharmaceuticae 1965, 17, 7-11—abstract.*
Mastalerz et al Journal of Organic Chemistry 2011, 76, 6389-6393.*
Roy et al Crystal Growth & Design 2011, 11, 4551-4558.*
Huang et al European Journal of Organic Chemistry 2012, 6586-6593.*
Abbott et al Journal of Materials Chemistry A: Materials for Energy and Sustainability 2013, 1, 11950-11960.*
Ghanem et al Advanced Materials 2014, 26, 6696-6700.*

* cited by examiner

*Primary Examiner* — David K O Dell
(74) *Attorney, Agent, or Firm* — James G. Shelnut; Charles R. Szmanda; The Patent Practice of Szmanda and Shelnut LLC (57) ABSTRACT

The present application for patent relates to novel electrochromic iptycene compounds and methods of their preparation. The application also provides for symmetrical and asymmetrical electrochromic iptycenes that can provide a full spectrum of color by manipulating their substituents.

9 Claims, 3 Drawing Sheets

ELECTROCHROMIC IPTYCENES

FIELD OF THE DISCLOSURE

The present application for patent relates to novel electrochromic iptycene compounds and methods of their preparation. The application also provides for electrochromic iptycenes that can provide a full spectrum of color by manipulating their substituents.

BACKGROUND

Electrochromism is a property displayed by some materials wherein the materials reversibly change color when an electronic charge is applied. Electrochromism occurs due to electrochemical redox reactions that take place at certain positions in the electrochromic materials. Various types of materials and structures can be used to construct electrochromic devices, depending on the specific applications Transition metal oxides represent a large family of materials possessing electrochromic properties. Among them, tungsten oxide, has been widely used in such applications as "smart glass".

Many organic materials exhibit redox states with distinct electronic (UV/visible) absorption spectra, wherein the switching of redox states generates new or different visible region bands. Color changes are commonly between a transparent, bleached state, where the chromophore only absorbs in the UV region, and a colored state. The switching may also be between two colored states.

Often, when there are more than two redox states which are electrochemically accessible in a given electrolyte solution, the electrochromic material may exhibit several colors and can be termed polyelectrochromic. As might be expected from the enormity of the field of organic chemistry, there are a vast number of organic compounds that exhibit electrochromism. Examples of well applied organic electrochromic materials are the viologens and conducting polymers such as polyacetylenes, poly(3-alkylthiophene)s, poly (3,4-alkylenedioxythiophene)s, often coupled with poly(styrenesulfonate), and polyaniline. Depending on the oxidation state polyaniline, for example, can be pale yellow, dark green, purple or black. Polymers based on triarylamine or carbazoles have also been used as organic electrochromic materials. Some organometallic materials such as metallopolymers and metallophthalocyanine also exhibit electrochromic behavior.

Iptycenes are cyclic materials that are built upon [2,2,2]-ring systems in which the bridges are aromatic rings. The simplest member of this class of compounds is triptycene, FIG. 1A. Iptycenes are unique materials in that they can provide steric blocking, which prevents interactions between various substituents of different molecules. This is especially important in chromophoric materials as interaction between chromophores that have a strong tendency to form non-emissive exciplex complexes when they interact is prevented or at least reduced. Iptycene materials are very stable and display solution-like emissive spectra and quantum yields in the solid state.

The three-dimensional shape of iptycenes creates interstitial space, or free volume, around the molecules. This space can confer size selectivity in sensory responses and also promotes alignment in oriented polymers and liquid crystals. Specifically, the iptycene containing polymers and molecules align in the anisotropic host material in a way that minimizes the free volume.

Structures that preserve high degrees of internal free volume can also be designed to create low dielectric constant insulators. These materials have high temperature stability (>500° C.) and hardness that make them useful in high temperature applications where other materials would not function properly.

The iptycene structures allow for small interpolymer motions, but at large deformations, the steric interactions between iptycenes result in the transfer of stress energy from one polymer to another. This mechanism has the ability to impart greater modulus, strength, and ductility. The use of iptycene structures is a promising approach to new generations of structural materials.

Thus there is an unmet need for electrochromic materials which provide a wide range of colors while having improved properties in solution and in applications.

SUMMARY OF THE DISCLOSURE

Disclosed and claimed herein are novel electrochromic iptycene compounds that can provide a full spectrum of colors by manipulating their substituents. Also disclosed and claimed herein are methods of preparing novel electrochromic compounds.

In a first embodiment, disclosed and claimed herein are compounds comprising an iptycene core which have three aromatic rings connected at two bridgeheads of the following general Structure 1:

Structure 1 comprising at least one of A, B and C, wherein A, B and/or C, when present, each comprising the same or different heterocyclic rings fused onto an aromatic rings of the iptycene wherein A, B, and C, when present, each further comprise the same or different aliphatic or aromatic substituents and wherein the compounds are capable of changing color when an electronic field is applied, wherein R and R' are the same or different and are H, an aliphatic, an aromatic or a heteroatom substituent.

In a second embodiment, disclosed and claimed herein are compounds of the above embodiment, wherein the heterocycles comprise at least one of oxygen, sulfur, selenium, tellurium, nitrogen, phosphorous, silicon, germanium, boron, aluminum and the transition elements of the periodic table and their derivatives.

In a third embodiment, disclosed and claimed herein are compounds of the above embodiments, wherein the substituents are the same or different and comprise saturated or unsaturated, substituted or unsubstituted aliphatic, cyclic or polycyclic aliphatic groups, aromatic, heterocyclic, fused aromatic or fused heteroaromatic groups or combinations thereof, and wherein the heterocyclic or fused heteroaromatic group comprises at least one of oxygen, sulfur, selenium, tellurium, nitrogen, phosphorous, silicon, germanium, boron, aluminum and the transition elements of the periodic table and their oxides.

In a fourth embodiment, disclosed and claimed herein are compounds of the above embodiments wherein at least one of A, B or C is a fused nitrogen-containing heterocycle.

In a fifth embodiment, disclosed and claimed herein are compounds of the above embodiments, wherein the heterocyclic ring is a pyridine In a sixth embodiment, disclosed and claimed herein are compounds of the above embodiments, wherein the substituents further comprise heteroatom linkages connecting the groups to themselves and/or to the fused heteroaromatic ring on the iptycene.

In a seventh embodiment, disclosed and claimed herein are compounds of the above embodiments, wherein the substituents may further comprise at least one of electron-withdrawing groups or electron-donating groups.

In an eighth embodiment, disclosed and claimed herein are compounds of the above embodiment, wherein at least one of the substituents comprises triarylamine, carbazole, furan, thiophene, or combinations thereof.

In a ninth embodiment, disclosed and claimed herein are compounds of the above embodiments, wherein the aryl group comprises at least one of a phenyl, fused phenyl, heterocycle, or fused heterocycle group or combinations thereof.

In a tenth embodiment, disclosed and claimed herein are compounds of the above embodiments, wherein at least one of the substituents comprises a non-aromatic heterocycle fused to an aromatic group.

In an eleventh embodiment, disclosed and claimed herein are compounds of the above embodiments, wherein the substituents may further comprise an iptycene.

In a twelfth embodiment, disclosed and claimed herein are compounds of the above embodiments, wherein at least one of A, B, or C, when present is part of a polymer.

In a thirteenth embodiment, disclosed and claimed herein are compounds of the above embodiments, wherein the compounds are capable of changing to more than one color when more than one electronic field strength is applied. In a fourteenth embodiment, disclosed and claimed herein are compounds of the above embodiments, further comprising at least one of a conductive metals wherein the metal is coordinated to the iptycene and/or the substituents.

In a fourteenth embodiment, disclosed and claimed herein are compounds of the above embodiments, further comprising at least one substituent that comprises at least one of a crosslinkable group and a polymerizable group.

In a fifteenth embodiment, disclosed and claimed herein are compounds of the above embodiments, further comprising at least one ionic salt material.

In a sixteenth embodiment, disclosed and claimed herein are compound of the above embodiments wherein the core triptycene comprises one to three heterocyclic compounds in place of one to three phenyl rings.

In a seventeenth embodiment, disclosed and claimed herein are compounds of the above embodiments wherein only one or two of the aromatic rings of the core triptycene are fused as shown in Structures 2 and 3 below, respectively:

Structure 2

Structure 3

DETAILED DESCRIPTION

As used herein, the conjunction "and" is intended to be inclusive and the conjunction "or" is not intended to be exclusive unless otherwise indicated. For example, the phrase "or, alternatively" is intended to be exclusive.

As used herein, the term "and/or" refers to any combination of the foregoing elements including using a single element.

As used herein the terms "composition" and "formulation" are used interchangeable and mean the same thing.

As used herein the term solvent means a liquid medium into which one or more of the various components of the formulations are soluble, colloidally suspended, or emulsified.

As used herein the term color refers not only to colors of different wavelengths, but also to colors of different intensities, such as, for example, light blues are different from darker blues.

As used herein the term aliphatic refers to branched or unbranched, saturated or unsaturated, cyclic or polycyclic alkanyl, alkenyl, or alkynyl groups and combinations such as, for example, methyl, ethyl, propyl, isopropyl, n-butyl, sec-butyl, tert-butyl, cyclohexyl, adamantly, and the like. The aforementioned groups may have substituents attached to its chain and/or onto its side groups. They may also contain heteroatom substitution in the chain, such as, for example, a diethylene oxide group which contain an oxygen heteroatom in the chain. Heteroatoms include, for example, oxygen, sulfur, selenium, tellurium, nitrogen, phosphorous, silicon, germanium, boron, aluminum and the transition elements of the periodic table and their derivatives, such as SO, $SO_2$, $S_x$, $SnH_2$, $N_x$, and the like, wherein x can be 2-6.

As used herein the term heterocycle alone or in combination refers to optionally substituted aromatic mono-radicals containing from about 4 to about 22 skeletal ring atoms, wherein one or more of the ring atoms is a heteroatom independently selected from among oxygen, nitrogen, sulfur, phosphorous, silicon, selenium, tellurium, silicon, germanium, boron, aluminum and the transition elements of the periodic table and there derivatives, such as for example, $S_x$, $N_x$, SO, $SO_2$ and $SiO_2$, but not limited to these atoms and the proviso that the ring does not contain two adjacent O or S atoms. Where two or more heteroatoms are present in the ring, in some embodiment, the two or more heteroatoms are the same and in some embodiments, some or all of the two or more heteroatoms are different. The term also includes optionally substituted fused and non-fused heteroaromatic radicals as described above having at least one heteroatom. In some embodiments, bonding to a heteroaromatic group is via a carbon atom of the heterocycle, and in some embodiments via the heteroatom of the ring. The heteroaromatic ring may be substituted on one or more or the carbon atoms or on one or more of the heteroatom when available. A fused heteroaromatic ring may contain between two to 4 fused rings. Heterocycles of the current disclosure include for example, the single ring, pyridyl; the fused rings, carbazolyl, benzimidazolyl, quinolinyl, acridinyl; and non-fused biheteroaryl, bipyridinyl. Further examples include furanyl, thienyl, oxazolyl, phenazinyl, benzofuranyl, benzoxazolyl, benzothiazolyl, benzothiadiazolyl, benzothiphenyl, benzoxadiazolyl, benzotriazolyl, imidazolyl, pyridazyl, pyrmidyl, pyrazinyl, pyrrolyl, pyrazolyl, purinyl, phthalazinyl, pteridinyl, quinolinyl, quinazolinyl, quinoxalinyl, triazolyl, tetrazoyl, thiazolinyl, triazinyl, thiadiazolyl, and he like and there derivatives, such as for example, their oxides.

Figure 1:
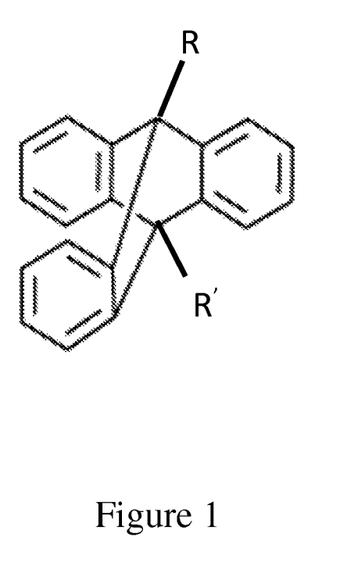
FIG. 1 shows the molecular structure of the basic triptycene molecule showing potential substitution at the bridgeheads.
Figure 3:
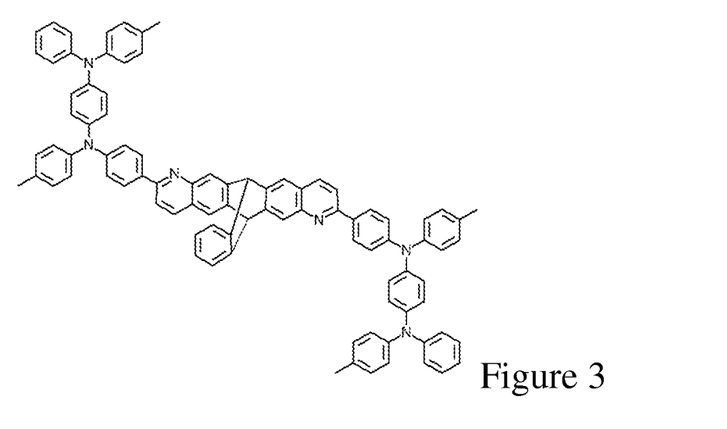
FIG. 3 is the molecular structure of a representative iptycene of the current disclosure with symmetrical arylamine substituents on only two fused rings.

Disclosed and claimed herein are novel electrochromic iptycene compounds and methods of their preparation. The application also provides for electrochromic iptycenes that can provide a full spectrum of color by manipulating their substituents. The basic core structure of iptycenes of the current disclosure is the triptycene molecule as shown in FIG. 1 showing three aromatic rings arrayed around centrally connected carbon bridgeheads. The three aromatic rings of the triptycene molecule may be the same or different. While FIG. 1 shows three phenyl groups arrayed in a triptycene arrangement, the compounds of the current disclosure are not limited to triptycenes with only phenyl rings. Other triptycene core molecules of the current disclosure include molecules that include one or more heterocyclic rings in place of the phenyl ring on FIG. 1, such as, for example, pyridine rings or pyrazine rings or other heterocycles as described herein. The molecules of the current disclosure further contain aromatic rings A, B and/or C fused to the one, two or all three of the aromatic rings of the core triptycene molecule. For example, FIG. 3 shows a molecule of the current disclosure with only two of the aromatic rings of the core triptycene being fused with heterocyclic rings. As shown in FIG. 1, the compounds disclosed and claimed herein may have bridge head substitutions, R and R' in the figure. R and R' may be the same or different and may be H, aliphatic, aromatic or heteroatom or other substituents as described in the current disclosure.

The fused aromatic rings A, B, and/or C, may be single heterocyclic materials or they may be multiply fused aromatic materials, one or more of which may be heterocyclic. The heterocyclic rings may contain one or more of oxygen, sulfur, selenium, tellurium, nitrogen, phosphorous, silicon, germanium, boron, aluminum and the transition elements of the periodic table and their derivatives, such as SO, $SO_2$, $S_x$, $SnH_2$, $N_x$, and the like, wherein x can be 2-6, in the ring system. The rings fused to the aromatic rings of the core triptycene may be the same or different in various embodiments of the current disclosure. The fused rings may be, for example, pyridine, carbazole, benzimidazole, quinoline, and acridine. Further examples include furan, thiophene, oxazole, phenazine, benzofuran, benzoxazole, benzothiazole, benzothiadiazole, benzothiobenzene, benzoxadiazole, benzotriazole, imidazole, pyridazole, pyrmidine, pyrazidinole pyrrole, prainyl, pyrazole, purine, phthalazine, pteridine, quinoline, quinazoline, quinoxaline, triazole, tetrazole, thiazoline, triazine, thiadiazole, and the like and combinations thereof.

The fused aromatic and/or heterocyclic rings on the triptycene may further contain substituents that can readily undergo redox reactions when a voltage is applied. The substituents can be the same or different and comprise aliphatic, unsaturated aliphatic, cyclic or polycyclic aliphatic, aromatic, heterocyclic, fused aromatic or fused heteroaromatic groups or combinations thereof, and wherein the heterocyclic or fused heteroaromatic group comprises at least one of nitrogen, sulfur, phosphorous, silicon, selenium, tellurium, silicon, germanium, boron, aluminum, oxygen or transition elements of the periodic table or their derivatives, such as, for example, oxides, sulfides, and the like. When discussing A, B and/or C in general, they are meant to include any substituents that may or may not be attached to them.

An example of a substituent suitable for the current disclosure include the representative structure shown in Structure 4 below showing a triarylamine derivative that is attached to the either the fused heterocycle of an iptycene or directly to the aromatic ring of the core iptycene.

Structure 4

Examples of substituents suitable for $Ar_1$ include substituted or unsubstituted aromatic and/or heterocyclic materials to which the heteroatom, in this case, nitrogen atoms, are attached. Aromatic or heterocyclic rings suitable as $Ar_1$ for the current disclosure are shown below are shown below in Structures 5 and 6:

Stuctures 5 wherein R is an aliphatic, aromatic, heterocyclic, electron-withdrawing or electron donating group. The unconnected straight lines in these structures represent potential attachment points.

Ar$_2$ are substituted or unsubstituted aromatic and/or heterocyclic groups attached to the heteroatom of the substituent. Examples of substituents suitable for Ar$_2$ in the current disclosure is shown in Structures 7 below, wherein X$_1$ is a substituent as described herein:

Structures 6

Structures 7

X$_1$ = H, Alkyl, t-Butyl, Alkoxy, wherein any one of $X_2$, $X_3$, $X_4$ or $X_5$ is a carbon or heteroatom as described herein, alone or in combination with other carbons or heteroatoms. Some examples of $X_1$ are shown but include halides, chalcogens, electron-withdrawing groups or electron-donating as are well known in the art and other substituents as described herein.

While Structure 4 shows one example of a substituent arrangement suitable for the current disclosure, Structures 8, shows other examples of suitable arrangements of substituents for compounds of the current disclosure:

Structures 8 wherein $Ar_3$ is the same or different than $Ar_1$ or $Ar_2$.

Other examples of suitable substituents are shown in Structures 9:

Structures 9 wherein $R_1$ and $R_2$ are the same or different and are substituted or unsubstituted carbon radicals or heteroatoms. The R groups can be halides, chalcogens and/or electron-withdrawing or electron-donating groups or other substituents as described herein well known in the art.

Other examples of suitable substituents are shown in Structure 10:

X = N, O, S wherein * is the point of attachment of the substituent.

The compounds of the current disclosure are electrochromic materials. Not to be held to theory, it is believed that when an electric current is passed through the triptycene the heteroatom is oxidized altering the configuration of the molecule and a resultant color change occurs. When a second heteroatom oxidize, either by an increase in the charge or by other methods, a second color change can occur, either a color of a different wavelength of a higher, or lower, tinctorial value. In this manner, different colors, or saturations, can be obtained. The iptycenes of the current disclosure can uniquely be constructed to give a full spectrum of colors by changing the substituents on the iptycene core molecule. Some substituents will provide one color, in a neutral state or in an oxidized state, and a different substituent can provide a different color in an oxidized state so that the combination of colors will be additive and a third color is obtained.

Figure 2:
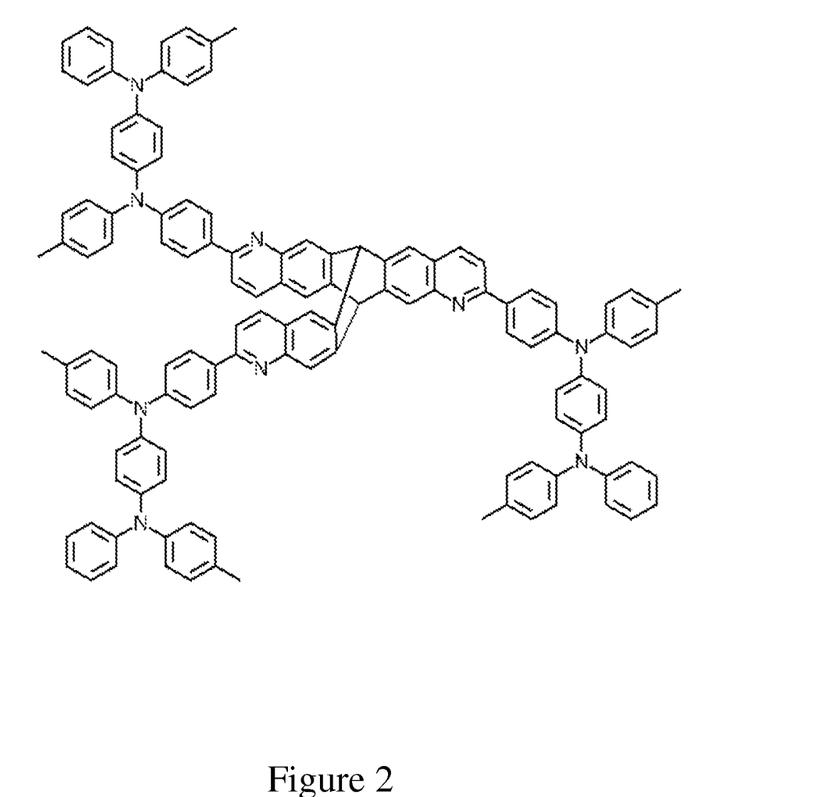
FIG. 2 is the molecular structure of a representative iptycene of the current disclosure with symmetrical arylamine substituents on three fused rings.

FIG. 2 illustrates an example of a symmetrical electrochromic iptycene of the current disclosure. There are a number of oxidizable sites on the molecule which, when exposed to an applied current, is capable of being oxidized to result in the molecule changing color. When a stronger current is applied more than one of the oxidizable sites oxidize and further color change can take place, so that, depending on the current applied, a spectrum of colors can be achieved as desired.

FIG. 3 illustrates an example of a triptycene of the current disclosure in which not all three of the aromatic rings of the triptycene core are fused. In this figure only two of the aromatic rings are fused. The ability to select the number of fused rings substituted on the aromatic rings allows for the manipulation of the molecule to provide a certain desired electrochromic property.

Figure 4:
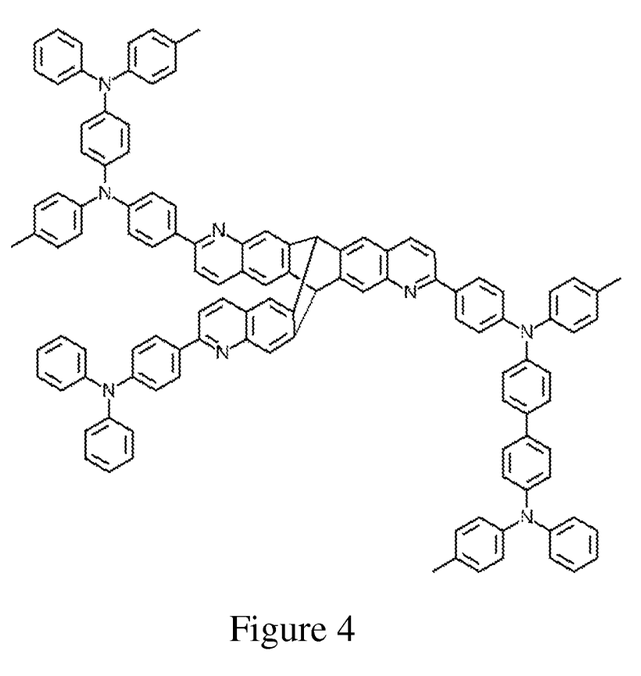
FIG. 4 is the molecular structure of a representative iptycene of the current disclosure with asymmetrical substituents substituted on each of the three fused rings.

FIG. 4 illustrates an example of an unsymmetrically substituted triptycene in which three different substituents are attached to the iptycene core. When oxidized by appli-

X = N, O, S where E can be:

Structures 10 cation of a voltage the triphenyl amine group becomes blue, the tetraphenylphenylene diamine becomes green and the dicarbazole substituent becomes orange, depending on the amount of voltage applied. In this manner, and by similar substitution strategies, a full spectrum of colors can be achieved.

The compounds of the current disclosure can be oxidized from neutral electronic states to one or more oxidized states under the application of an appropriate electric field or voltage. The compounds of the current disclosure are reversible in that various oxidation states are chemically and electronically stable and can be converted to other lower or higher oxidation states, even the original neutral electronic state, using a reverse electric field in smaller, equal, or larger magnitude to the electric field used to oxidize the molecules initially. As a result, each of the achievable electronic states, both neutral and oxidized, are reversible and interchangeably achieved using specific applied electric fields to oxidize or reduce the current electronic states in order to achieve the characteristic colors of each achievable electronic state. As desired oxidation may purposely be held at specific electric field strengths so the molecule maintains a specific coloration.

Compounds of the current disclosure may contain more than one iptycene core as shown in Structure 11 below:

Structure 11

Here one of the aromatic rings of a triptycene serves as an aromatic ring of a second triptycene. Any and all of the aromatic groups of one triptycene may also function as the aromatic ring for other triptycenes. As well, the connecting of aromatic rings from one iptycene by another iptycene may provide an oligomeric or polymeric material where a number of triptycene functionalities are formed.

Compounds of the current disclosure may be a monomer or an iptycene polymer as described above. The iptycene may also be part of polymer in which one or more of the substituents of the triptycene is part of a polymer backbone, such as, for example, one of the aromatic groups of the triptycene is linked to the aromatic group of another triptycene and so on. The connection may be by direct bonding of the aromatic groups to each other or there may be a connection group, such as, for example, a heteroatom, which may have redox properties of a saturated or unsaturated connecting group, such as, for example, an aromatic group, a heterocyclic group, an olefin, an acetylene, or combinations thereof. In this manner further tailoring of the color changes during the redox application of an electronic current can occur, as desired. The compounds of the current disclosure may also be side groups of polymers. For example, an electrochromic triptycene may be an ester group of a polyacrylate ester.

The compounds of the current disclosure may further contain, as substituents, one or more free radical induced polymerizable materials, such as, for example, an acrylate, a methacrylate, an alkyne, or a vinyl material. In the presence of a free radical, generated either thermally or photolytically or both, the substituent will react with each other to form an oligomer or polymer, as is well known in the art.

Other compounds of the current disclosure may further contain, as substituents, one or more acid or base catalyzed crosslinkable materials, such as, for example, acid or base catalyzed crosslinkable materials such as, the aminoplasts, such as monomeric or oligomeric methoxymethyl melamines, guanamines, methylols, monomeric or oligomeric glycolurils, hydroxy alkyl amides, blocked isocyanates, and divinyl monomers. Other examples include, for example, epoxies, oxetanes, furan, thiiranes, thietanes and the like. When an acid or a base is generated, either thermally or photolytically or both, the substituent will react with each other to form an oligomer or polymer or crosslinked material, as is well known in the art.

Compounds of the current disclosure may further contain ionic salt structures. These salts may be integral to the iptycene material. For example, a heterocyclic ring fused to the aromatic rings of the triptycene core may be in the form or a salt, such as, for example, a fused pyridinium salts. The salt structure may be coordinated with various structures on the iptycene, such as a substituent that acts as a ligand that can coordinate a salt structure. Salts include, for example alkali salts, alkaline earth salts, nitrogen salts, including for example, nitrogen aliphatic and aromatic heteroatom rings, sulfur salts such as for example sulfonium, sulfinium and sulfenium salts, boron containing salts, halide salts and the like as are known in the art.

The iptycene functionality of the compounds of the current disclosure, as previously stated, provide for a three-dimensional shape which creates interstitial space, or free volume, around the molecules. The current disclosure provides for these spaces to be occupied by metals, conductive metals, ionic species, organic molecules, conductive polymers, fullerenes, caped or uncapped carbon nanotubes, graphene materials or other materials which can increase or decrease conductivity as desired, or that may be selected to alter the color spectrum during application of an electronic charge.

The three dimensional structure of the iptycene helps to prevent interaction, not only with chromophores, but with the other portions of the molecule reduction the tendency to crystallize. This property allows for improvements in solubility, as compared to the currently available electrochromic materials, in desirable solvents such as those whose toxicity is low compared to solvents required to solubilize non-iptycene electrochromic materials. The high solubility of the current compounds allows them to be dissolved and blended into transparent or opaque, liquid or solid-state electrolytic matrices, where other electrochromic materials would not function. The increase in solubility also allows for a broadening of process capabilities. For example formulations containing the current compounds allow for solution based coating application, such as, for example, screen printing, lithographic printing, flexographic printing, spinning, dip coating, electrostatic spray coating, curtain coating, roller coating, bar coating, web-spinning and the like. The electrochromic iptycene also provide for high temperature application, with thermal stability >300° C. as well as increased hardness. Both properties allow for electrochromism to be used in environment unobtainable with the currently available electrochromic materials.

The compounds of the current disclosure can be used to prepare glass coating, such as those electrochromic materials used for smart glass, plastic coatings and fabric coatings. Because of their unique physical properties the compounds of the current disclosure can be used in formulations to make plastic sheets in which the entire sheet is electrochromic, not only a coating applied to a plastic sheet. Additionally the compounds can be included in fiber compositions and formed into electrochromic fibers, fabrics, and other wearable configurations and devices

EXAMPLES

Scheme 1 illustrates a method of preparation for a representative symmetrical electrochromic triptycene of the current disclosure wherein all three aromatic rings of the triptycene are fused with heterocyclic substituents:

tycene (Luminescence Technology Corp, Taiwan) and 0.114 g (0.800 mmol) of $NaSO_4$ in 10 mL of dichloromethane was refluxed for 1 hr under stirring (1-3 drops of 1 M HCl can be added to help catalyze formation of the imine intermediate). During this 1 hr period, the yellow colored solution changed to an orange-red color. At this point, 0.069 g (0.689 mmol) of ethylvinyl ether and 10 mol % of $I_2$ in 10 mL of THF were added to the reaction mixture. The resultant mixture was refluxed for 8 hr. After the completion of the reaction, as indicated by TLC, the reaction mixture was quenched with 10 mL of a 5% sodium thiosulfate aqueous solution ($Na_2S_2O_3 \cdot 5H_2O$). The compound was extracted with ethyl acetate, dried over anhydrous $Na_2SO_4$, and concentrated under reduced pressure. The product was purified by column chromatography on a short plug of silica gel (hexanes/ethyl acetate=5:1).

Scheme 1

Synthesis 1

In a round bottom flask equipped with a magnetic stirring bar, a mixture of 0.300 g (0.640 mmol) of compound A in Scheme 1, 0.064 g (0.214 mmol) of 2,6,14-triaminotrip- Scheme 2 illustrates a method of preparation for a representative electrochromic triptycene of the current disclosure wherein only two of the aromatic rings of the triptycene contain fused heterocyclic substituents:

Scheme 2

Compound A

Synthesis 2

In a round bottom flask equipped with a magnetic stirring bar, a mixture of 0.300 g (0.640 mmol) of compound A in Scheme 2, 0.091 g (0.320 mmol) of 2,6-diaminotriptycene (Luminescence Technology Corp, Taiwan) and 0.114 g (0.800 mmol) of $NaSO_4$ in 10 mL of dichloromethane was refluxed for 1 hr under stirring (1-3 drops of 1 M HCl can be added to help catalyze formation of the imine intermediate). During this 1 hr period, the yellow colored solution changed to an orange-red color. At this point, 0.070 g (0.699 mmol) of ethylvinyl ether and 10 mol % of $I_2$ in 10 mL of THF were added to the reaction mixture. The resultant mixture was refluxed for 8 hr. After the completion of the reaction, as indicated by TLC, the reaction mixture was quenched with 10 mL of a 5% sodium thiosulfate aqueous solution ($Na_2S_2O_3 \cdot 5H_2O$). The compound was extracted with ethyl acetate, dried over anhydrous $Na_2SO_4$, and concentrated under reduced pressure. The product was purified by column chromatography on a short plug of silica gel (hexanes/ethyl acetate=5:1).

Scheme 3 illustrates a method of preparation for a representative asymmetrical electrochromic triptycene of the current disclosure wherein all three aromatic rings of the triptycene are fused with heterocyclic substituents:

Scheme 3

Compound B

-continued

Synthesis 3

In a round bottom flask equipped with a magnetic stirring bar, a mixture of 0.100 g (0.184 mmol) of compound B in Scheme 3, 0.071 g (0.182 mmol) of 2,6,14-triaminotriptycene, (Luminescence Technology Corp, Taiwan) and 0.114 g (0.800 mmol) of $NaSO_4$ in 10 mL of dichloromethane was refluxed for 1 hr under stirring (1-3 drops of 1 M HCl can be added to help catalyze formation of the imine intermediate). During this 1 hr period, the yellow colored solution changed to an orange-red color. Imine formation was confirmed on thin layer chromatography. At this point, 0.050 g (.183 mmol) of 4-(diphenylamino)benzaldehyde dissolved in 2 mL of dichloromethane was added to the mixture and refluxed for 1 hr under stirring. Formation of the second imine was confirmed on thin layer chromatography. Finally, 0.085 g (0.181 mmol) of compound A in Scheme 3 dissolved in 2 mL of dichloromethane was added to the mixture and refluxed for 1 hr under stirring. Formation of the third imine was confirmed on thin layer chromatography.

Following the formation of the third imine, 0.058 g (0.579 mmol) of ethylvinyl ether and 10 mol % of 12 in 10 mL of THF were added to the reaction mixture. The resultant mixture was refluxed for 8 hr. After the completion of the reaction, as indicated by TLC, the reaction mixture was quenched with 10 mL of a 5% sodium thiosulfate aqueous solution ($Na_2S_2O_3.5H_2O$). The compound was extracted with ethyl acetate, dried over anhydrous $Na_2SO_4$, and concentrated under reduced pressure. The product was purified by column chromatography on a short plug of silica gel (hexanes/ethyl acetate=5:1).

Compounds of the current disclosure can be used for electrochromically tinting of paint resulting in electrochromic coating. Due to their ability to solubilize readily in standard solvents and as emulsions or dispersions, tailoring of colors of the paint and coating can be obtained, such as, for example, opaque white to a desired color when a voltage is applied.

The compounds can be used in self-powered electrochromic devices such as, for example, energy transducers, organic photovoltaics, piezoelectronics, and the like. While electrochromic materials are used to provide colors in thee visible region of the electromagnetic spectrum, the compounds of the current disclosure may be used to change their spectrum in the UV and/or infrared (IR) region, such as, for example, the near infrared (NIR) region. NIR applications include identification of friend and foe, energy absorption, IR pyroelectrics, IR filtrations, radar and the like.

We claim:
1. Compounds comprising an iptycene core of the following general configuration:

comprising at least one of A, B and C, wherein A, B and C, when present, comprises a pyridine ring fused onto an aromatic ring of the iptycene, wherein A, B, and C, when present, each further comprise the same or different aliphatic or aromatic substituents, wherein at least one of the substituents comprises a triarylamine, a carbazole, a furan, or a thiophene; wherein R and R' are the same or different and are H, an aliphatic group, an aromatic group or a heteroatom, and wherein the compounds are capable of changing color when an electronic field is applied.

2. The compounds of claim 1, wherein the aliphatic substituents comprise saturated or unsaturated, substituted or unsubstituted aliphatic, cyclic or polycyclic aliphatic groups.

3. The compounds of claim 1, wherein the aromatic substituents comprise at least one of a phenyl, fused phenyl, heterocycle, or fused heterocycle group or combinations thereof.

4. The compounds of claim 3, wherein the heterocycles or fused heterocycles are comprised of at least one of oxygen, sulfur, sulfoxide, sulfur dioxide, selenium, tellurium, nitrogen, phosphorous, silicon, silicon oxide, germanium, boron, or aluminum.

5. The compounds of claim 1, wherein the aliphatic and aromatic substituents further comprise heteroatom linkages connecting the substituents to the pyridine ring fused onto the iptycene core.

6. The compounds of claim 1, wherein the substituents may further comprise a second iptycene.

7. The compounds of claim 1, wherein at least one of A, B, and C is part of a polymer.

8. The compounds of claim 1, further comprising at least one conductive metal wherein the metal is coordinated to the iptycene and/or to the substituents.

9. The compounds of claim 1, further comprising at least one ionic salt material.

* * * * *